United States Patent [19]
Smedley et al.

[11] Patent Number: 5,390,898
[45] Date of Patent: Feb. 21, 1995

[54] NEEDLELESS DUAL DIRECTION CHECK VALVE

[75] Inventors: William H. Smedley, Lake Elsinore; Terry M. Haber, El Toro; Clark B. Foster, Laguna Niguel, all of Calif.

[73] Assignee: Habley Medical Technology Corporation, Laguna Hills, Calif.

[21] Appl. No.: 223,058

[22] Filed: Apr. 6, 1994

[51] Int. Cl.⁶ ............................................. F16L 37/28
[52] U.S. Cl. ..................... 251/149.6; 604/256; 604/905; 251/149.1
[58] Field of Search ............ 251/149.6, 149.1; 604/256, 905

[56] References Cited

U.S. PATENT DOCUMENTS

| | | | |
|---|---|---|---|
| 4,421,296 | 12/1983 | Stephens | 251/149.6 |
| 4,700,744 | 10/1987 | Rutter et al. | 251/149.6 |
| 4,710,168 | 12/1987 | Schwab et al. | 251/149.1 |
| 4,819,908 | 4/1989 | Norkey | 251/149.6 |
| 5,289,849 | 3/1994 | Paradis | 251/149.1 |

Primary Examiner—A. Michael Chambers
Attorney, Agent, or Firm—Hawes & Fischer

[57] ABSTRACT

A dual direction check valve which facilitates the connection of an IV fluid line to the proximal end of a hypodermic needle that is used to make a veni puncture so that a patient may be infused with fluid from an IV medication bag, or the like. What is more, the check valve is adapted to reliably block the backflow of blood through the needle during the interconnection and start-up of the IV system. A resilient valve core formed from an elastomeric material has a peripheral sealing surface extending therearound. The check valve is closed to fluid flow in both directions when the sealing surface of the valve core mates against a complementary peripheral sealing surface which surrounds the valve core. The check valve is opened to fluid flow in both directions when an axial pushing force (e.g. generated by a Luer lock fitting) is applied to the valve core, whereby the valve core is compressed and the sealing surface thereof is separated from its complementary sealing surface to establish a gap therebetween.

9 Claims, 3 Drawing Sheets

NEEDLELESS DUAL DIRECTION CHECK VALVE

BACKGROUND OF THE INVENTION

1. Field of the Invention

A two-way check valve having particular application to facilitate the connection of a syringe or an IV fluid line to the proximal end of a needle so that a veni puncture can be made through a patient's tissue while the flow of fluid between the syringe or IV line and the needle in both proximal and distal directions through the check valve may be reliably controlled.

2. Prior Art

IV systems have long been used in the medical field to deliver a timed supply of one or more medicines, solutions, and the like to a patient. In order to start the IV, the healthcare worker typically uses a hypodermic needle to make a veni puncture through the patient's tissue. The hypodermic needle is often taped to the puncture site (e.g. the patient's arm) to insure stability and prevent an accidental detachment of the needle from the vein. Then, an IV fluid line is coupled to the exposed proximal end of the needle in order to place the needle in fluid communication with an IV medication bag or similar fluid source.

However, prior to coupling the IV fluid line to the needle, the patient's blood may rush unchecked from the vein and through the needle to leak out the open proximal end thereof. This backflow of blood (sometimes referred to as backflash) through the needle has been known to expose healthcare workers to infection with a contagious disease, such as AIDS, hepatitis, or the like, as a consequence of treating a patient with a blood related disease.

It would therefore be desirable to have available a reliable two-way check valve to permit fluid communication between an IV medication bag and a hypodermic needle while also preventing blood backflash through the needle during the connection of the IV fluid system.

SUMMARY OF THE INVENTION

A two-way check valve is described which enables the connection of a syringe or an IV fluid line from an IV infusion system to a hypodermic needle that penetrates a patient's tissue. The check valve includes opposing proximal and distal housing members that are connected together to form a bi-directional fluid path therethrough. The proximal housing member has a female docking port at one end thereof within which to receive a standard Luer lock tip from the syringe or fluid line. The distal housing member has a male docking port at one end thereof that facilitates coupling the check valve to the hypodermic needle. The proximal housing member encloses a pressure cap and an elastomeric valve core. The pressure cap has a plurality of force transmitting pads spaced evenly therearound to be engaged by an incoming Luer lock tip. The pressure cap is anchored to the valve core so that a distal pushing force applied to the force transmitting pads of the pressure cap is transferred to the valve core. The valve core has a peripheral fluid sealing surface extending completely therearound which, in the normally closed condition of the check valve, is mated flush against a complementary peripheral fluid ceiling surface which extends completely around the proximal housing member so that a 360 degree fluid-tight seal is formed at the interface of the fluid sealing surfaces, whereby to reliably block the flow of fluid in both the proximal and distal directions through the check valve.

When the Luer lock tip is moved through the female docking port of the proximal housing member and into contact with the force transmitting pads of the pressure cap, the axial pushing force generated by the Luer lock tip and applied to the pressure cap is correspondingly transferred to the elastomeric valve core so as to compress (i.e. deform) the valve core between the pressure cap and the distal housing member located therebelow. Accordingly, the fluid sealing surface of the valve core is moved distally relative to the fluid sealing surface of the proximal housing member, whereby to establish a gap between the sealing surfaces and thereby open the bi-directional fluid path through the check valve. When the Luer lock tip is removed from the female docking port of the proximal housing member, the compressive pushing force generated thereby and applied to the elastomeric valve core is similarly removed. Hence, and by virtue of its characteristic spring-like memory, the valve core will regain its original, prestressed shape, whereby the fluid sealing surface thereof will once again be mated flush against the complementary fluid sealing surface of the proximal housing member to reestablish the 360 degree seal by which to reliably block the flow of fluid through the check valve in both the proximal and distal directions.

DETAILED DESCRIPTION

Figure 1:
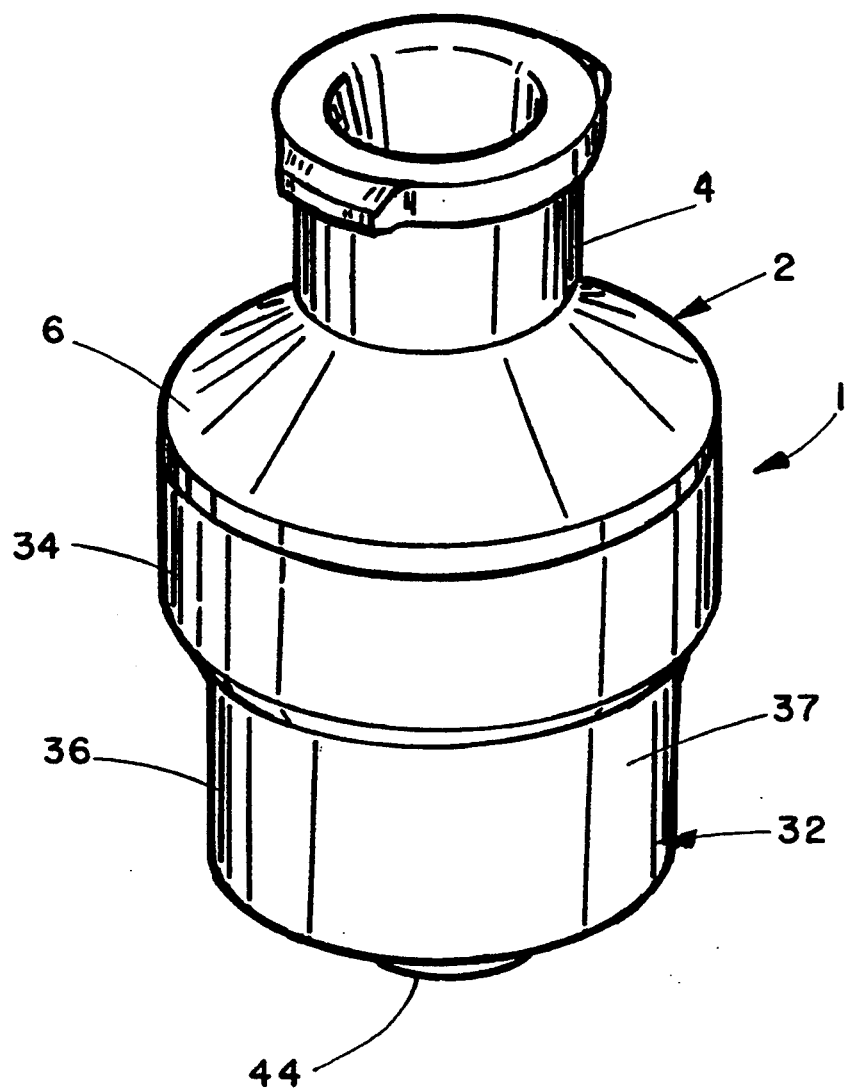
FIG. 1 shows the needleless, dual direction check valve which forms the present invention.
Figure 2:
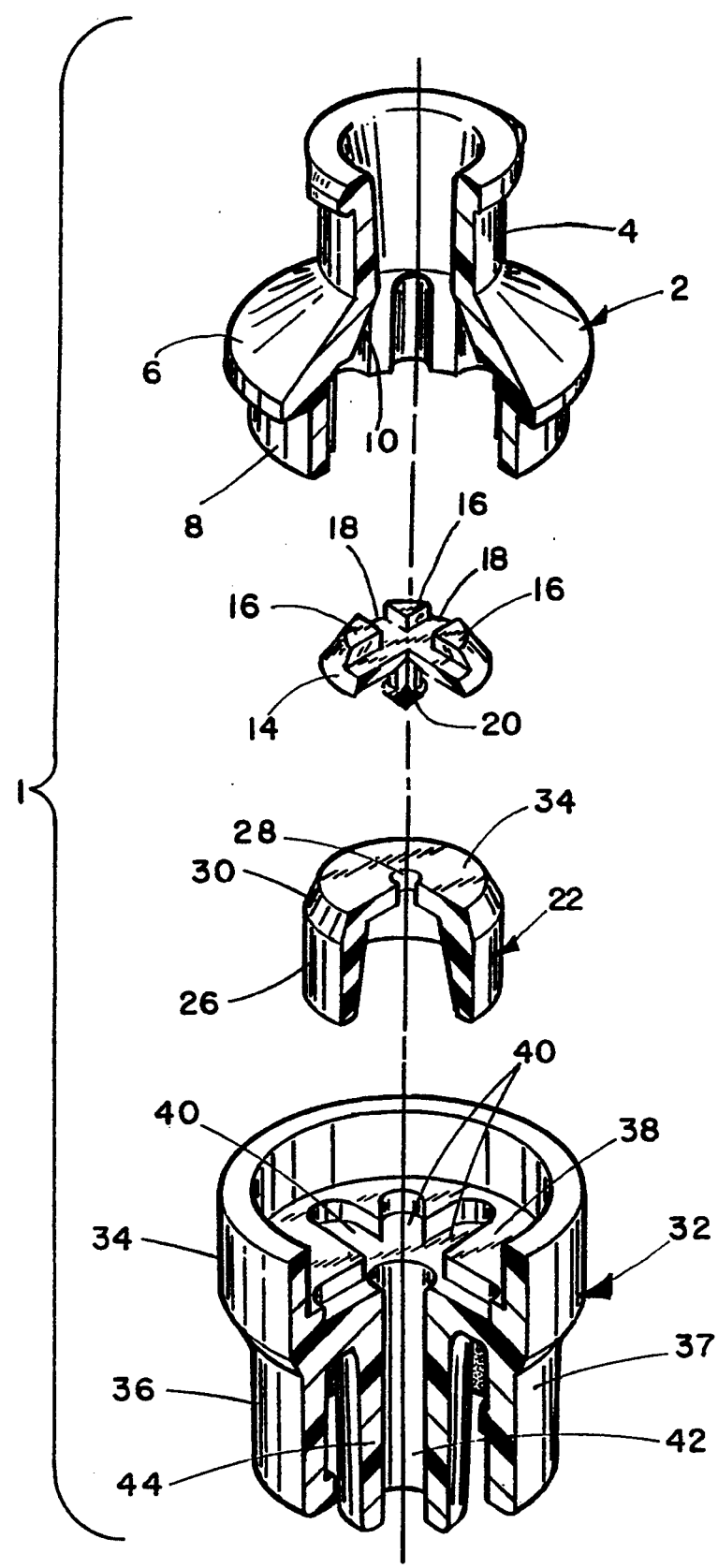
FIG. 2 is an exploded view, in partial cross-section, of the check valve of FIG. 1.

The needleless check valve 1 which forms the present invention is initially described while referring concurrently to FIGS. 1 and 2 of the drawings. The check valve 1 includes a proximal housing member 2 having a cylindrical female docking port 4 at one end thereof. Female docking port 4 is sized to receive therewithin a conventional Luer lock tip (best shown in FIGS. 3 and 4) that is common to many fluid infusion devices, such as a syringe, an IV fluid line, or the like. Located at the opposite end of the proximal housing member 2 from docking port 4 is a closure including a conical skirt 6 and a cylindrical connector ring 8. The conical skirt 6 flares outwardly from the docking port 4, and the cylindrical connector ring 8 projects downwardly (i.e. distally) from the skirt 6. As will be disclosed in greater detail hereinafter when referring to FIGS. 3 and 4, the proximal housing member 2 carries a peripheral fluid sealing surface 10 located at the interior of skirt 6 which cooperates with a complementary peripheral sealing surface of a soon to be described valve core 22 to control the flow of fluid through the check valve 1.

A rigid (e.g. hard plastic) pressure cap 12 is surounded by the proximal housing member 2 so that a distally directed pushing force applied to the pressure cap 12 by a Luer lock tip moving through the female docking port 4 of housing member 2 is transmitted to valve core 22 by pressure cap 12. Pressure cap 12 includes a generally disk-like base 14 having a plurality of force transmitting pads 16 spaced evenly from one another around the top thereof so that a corresponding plurality of fluid ducts 18 are established in the spaces between the force transmitting pads 16. Projecting downwardly from the base 14 of pressure cap 12 is a locking barb 20 by which the pressure cap 12 is securely attached to the valve core 22.

The valve core 22 which, in the assembled configuration of FIG. 1 (but best shown in FIGS. 3 and 4), is disposed in concentric alignment with and surrounded by the proximal housing member 2 is formed from an elastomeric (e.g. soft rubber) material having a spring-like memory. Valve core 22 includes a flat, force receiving head 24 and a neck 26 depending downwardly from the head. A hole 28 is formed through the center of the head 24 and adapted to receive therethrough and capture the locking barb 20 of the pressure cap 12. Therefore, with the locking barb 20 of pressure cap 12 pushed through the hole 28 in the head 24 of valve core 22, the disk-like base 14 of pressure cap 12 is anchored flush against the head 24 of valve core 22 so that the aforementioned distal pushing force applied to the force transmitting pads 16 of cap 12 from a Luer lock tip received by housing member 2 will be reflected in the deformation of the neck 26 of the elastomeric valve core 22.

A peripheral sealing surface 30 extends around the valve core 22 between the force receiving head 24 and neck 26 thereof. As will also be disclosed in greater detail when referring to FIGS. 3 and 4, the sealing surface 30 of valve core 22 cooperates with and is movable relative to the sealing surface 10 of the proximal housing member 2 to control the flow of fluid through the check valve 1.

The check valve 1 also includes a distal housing member 32 that is bonded to the proximal housing member 2 to complete a fluid flow path through the valve 1. The distal housing member 32 includes a cylindrical connector ring 34 that, in the assembled configuration of FIG. 1 (but best shown in FIGS. 3 and 4), is mated in surrounding engagement to the connector ring 8 of proximal housing member 2, whereby the proximal and distal housing members 2 and 32 are securely connected together. Depending downwardly (i.e. distally) from the connector ring 34 of housing member 32 is a male docking port 36.

The male docking port 36 of distal housing member 32 has a flat valve seat 38 extending thereacross. In the assembled valve configuration of FIG. 1 (but best shown in FIGS. 3 and 4), the neck 26 of valve core 22 rests upon and is supported by valve seat 38 of docking port 36 so that the distal movement of valve core 22 through check valve 1 is limited in response to a distal pushing force applied thereto via pressure cap 12. In addition, a plurality of fluid collecting openings 40 are formed in the valve seat 38. The fluid collecting openings 40 project radially outward from and communicate with a fluid passage 42 that extends longitudinally through the male docking port 36 of distal housing member 32.

The male docking port 36 of distal housing member 32 includes an outer cylindrical wall 37 that surrounds an inner cylindrical wall 44, such that outer and inner walls 37 and 44 of docking port 36 depend from valve seat 38 in spaced coaxial alignment with one another. The outer wall 37 is preferably threaded, and the inner wall 44 is preferably tapered in order to form a Luer lock fitting to facilitate connection between the check valve 1 and a hypodermic needle (not shown) so as to permit fluid communication therebetween via the longitudinal fluid passage 42 through docking port 36.

Figure 3:
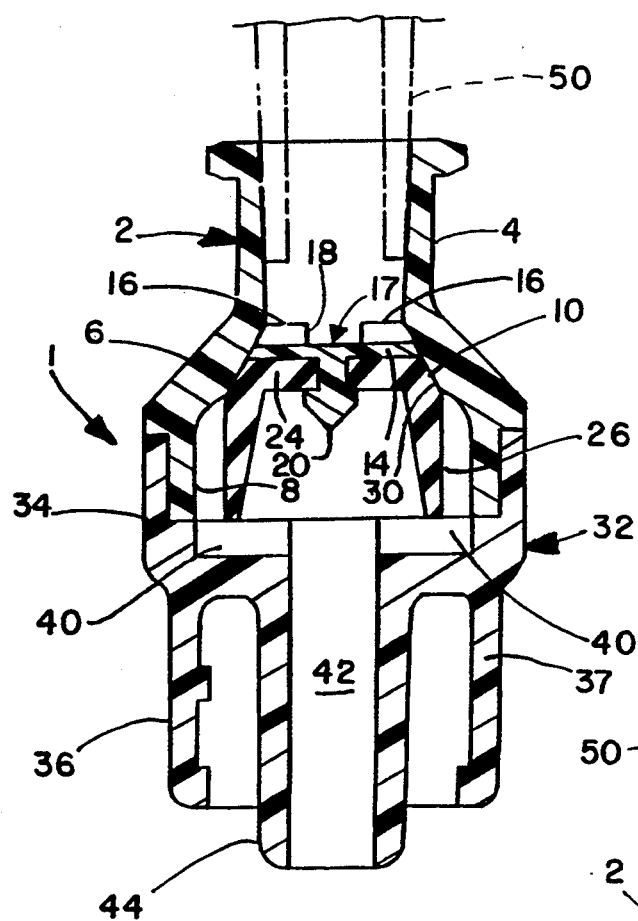
FIG. 3 is a cross-section of the check valve in the normally closed condition to block the flow of fluid in proximal and distal directions therethrough.
Figure 4:
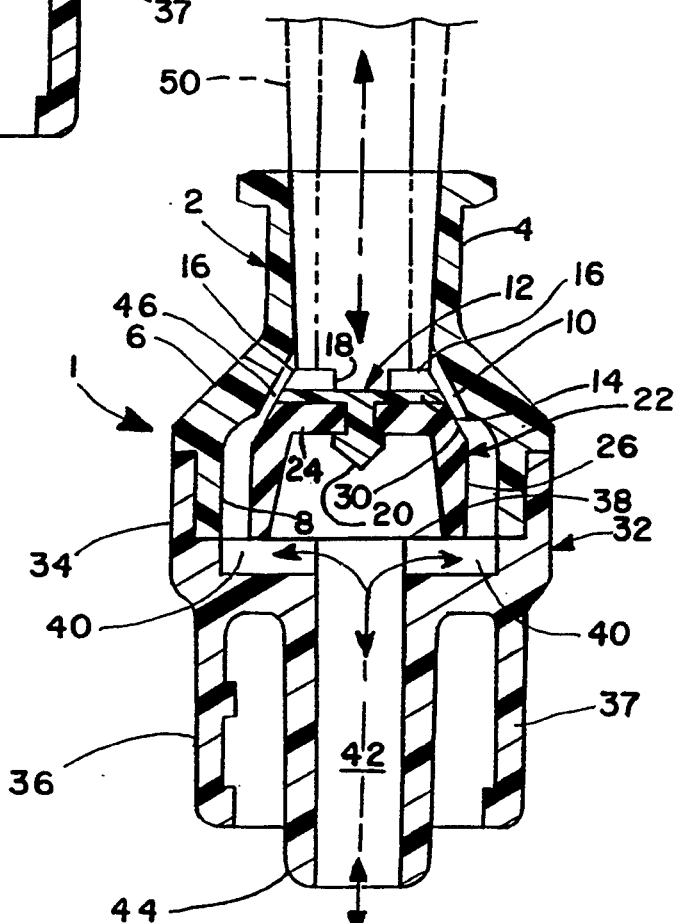
FIG. 4 is a cross-section of the check valve in the open condition to permit two-way fluid flow therethrough.

The operation of the needleless check valve 1 of this invention is now explained while referring to FIGS. 3 and 4 of the drawings. In the closed check valve condition of FIG. 3, prior to the movement of a Luer lock tip (designated 50 and shown in phantom lines) through the female docking port 4 of proximal housing member 2 and into contact with the force transmitting pads 16 atop pressure cap 12, the proximal housing member 2 and the valve core 22 cooperate with one another to interrupt the flow of fluid through check valve 1.

More particularly, in the closed condition, the elastomeric valve core 22 is in a relaxed state, inasmuch as no distal pushing (i.e. compressive) force is being applied thereto. Therefore, the neck 26 of valve core 22 which is resting upon the valve seat 38 of distal housing member 32, retains its original shape. Accordingly, the peripheral sealing surface 30 of valve core 22 is received flush against the complementary peripheral fluid sealing surface 10 below the skirt 6 of the proximal housing member 2, whereby a reliable 360 degree fluid-tight seal is formed around the check valve 1. Hence, the check valve 1 is normally biased in the closed condition of FIG. 3 such that the flow of fluid between the docking port 4 of proximal housing member 2 and the fluid passage 42 of distal housing member 32 will be blocked at the interface of the fluid sealing surfaces 10 and 30.

In the open check valve condition of FIG. 4, a Luer lock tip 50 (from a conventional syringe or IV line) is now moved through the female docking port 4 of proximal housing member 2 into contact with the force transmitting pads 16 atop pressure cap 12 to apply a corresponding distal pushing force thereto. Since the pressure cap 12 is anchored to the valve core 22 by means of locking barb 20, the distal pushing force applied to force transmitting pads 16 is transferred by way of the base 14 of pressure cap 12 to the adjacent force receiving head 24 of valve core 22 to cause the neck 26 of the elastomeric valve core to be compressed between the base 14 of pressure cap 12 and the valve seat 38 of distal housing member 32. Accordingly, the valve core 22 will be deformed whereby to completely open the former fluid-tight seal created at the interface of the respective peripheral fluid sealing surfaces 10 and 30 of the proximal housing member 10 and the valve core 22.

More particularly, the aforementioned compression of valve core 22 in response to the distal pushing force generated by Luer lock tip 50 causes the peripheral fluid sealing surface 30 thereof to move downwardly (i.e. distally) relative to the opposing proximal fluid sealing surface 10 below the skirt 6 of proximal housing member 10 such that a gap 46 is established between the fluid sealing surfaces 10 and 30. Therefore, a fluid path (shown dotted) is opened between the Luer lock tip 50 at the docking port 4 of proximal housing member 2 and the longitudinal fluid path 42 through the distal housing member 32 via the fluid ducts 18 of pressure cap 12, the gap 46 between sealing surfaces 10 and 30, and the radially extending fluid collecting openings 40 formed in the valve seat 38 of distal housing member 32.

However, it is to be understood that the fluid flow path (as indicated by the dotted lines in FIG. 4) that is opened through check valve 1 in the open valve condition is bi-directional from Luer lock tip 50 to fluid passage 42, and vice versa. Moreover, with the two-way check valve 1 in the closed condition of FIG. 3, fluid flow therethrough in both the proximal and distal directions will be effectively blocked whether or not a Luer lock tip 50 is disposed in female docking port 4. In this same regard, it may also be appreciated that backflow of a patient's blood through check valve 1 and the possible spread of contagious disease are avoided during the time that an IV fluid line is attached to the female docking port 4.

When the Luer lock tip 50 is removed from the female docking port 4 of proximal housing member 2, the distal pushing force generated by tip 50 and applied to the valve core 22 by way of pressure cap 12 is similarly removed. The spring-like memory that is characteristic of the elastomeric valve core 22 will cause the neck 26 of valve core 22 to automatically recover from its compressed shape (shown in FIG. 4) to its normally relaxed shape (shown in FIG. 3). Accordingly, the 360 degree fluid seal between the respective fluid sealing surfaces 10 and 30 of proximal housing member 2 and valve core 22 will be reestablished around the two-way check valve 1 so that the valve is once again adapted to block the flow of fluid therethrough.

It will be apparent that while a preferred embodiment of the invention has been shown and described, various modifications and changes may be made without departing from the true spirit and scope of the invention.

Having thus set forth the preferred embodiment, what is claimed is:

1. A check valve having a fluid receiving end, a fluid expulsing end, a fluid path extending between said fluid receiving and expulsing ends, and comprising:
    a first sealing surface located in said fluid path;
    a valve core to control the flow of fluid through the fluid path of said check valve, said valve core being formed from a spring-like elastomeric material and having a second sealing surface, said valve core being compressed in response to an axial pushing force applied thereto for causing said valve core to move in said fluid path from a closed valve position where said first and second sealing surfaces engage one another to block said fluid path and prevent the flow of fluid through said check valve to an open valve position where said second sealing surface is spaced from said first sealing surface to establish a gap therebetween and thereby open said fluid path to the flow of fluid through said check valve, and
    a rigid pressure cap affixed to said elastomeric valve core for receiving the axial pushing force and transferring said pushing force to said valve core for compressing said valve core and thereby causing said valve core to move in said fluid path.

2. The check valve recited in claim 1, wherein said second sealing surface extends around the periphery of said valve core.

3. The check valve recited in claim 1, wherein said fluid receiving end includes a female docking port, said axial pushing force being applied to said rigid pressure cap through said female docking port for compressing said valve core and causing said valve core to move in said fluid path.

4. The check valve recited in claim 1, wherein said pressure cap has a plurality of force transmitting pads spaced from one another for receiving the axial pushing force and transferring said pushing force to said valve core, said pressure cap also having a corresponding plurality of fluid ducts formed between said force transmitting pads and located in the fluid path of said check valve between said fluid receiving and expulsing ends.

5. The check valve recited in claim 1, wherein said fluid expulsing end includes a seat extending thereacross, said valve core resting upon said seat so as to be compressed between said pressure cap and said seat in response to the axial pushing force received by said pressure cap.

6. The check valve recited in claim 5, wherein said fluid expulsing end also includes a fluid passage extending longitudinally therethrough and located in said fluid path.

7. The check valve recited in claim 6, wherein said fluid expulsing end also includes a plurality of fluid collection openings extending radially through said seat and located in said fluid path in fluid communication with said longitudinally extending fluid passage.

8. The check valve recited in claim 6, wherein said fluid expulsing end also includes a male Luer lock fitting surrounding said longitudinally extending fluid passage.

9. The check valve recited in claim 1, wherein said elastomeric valve core is made from rubber.

* * * * *